United States Patent [19]

Fleckenstein et al.

[11] 4,157,288
[45] Jun. 5, 1979

[54] POLAROGRAPHIC MEASURING PROBE WITH DIFFUSION FILM MEMBRANE

[75] Inventors: Wolfgang Fleckenstein, Kiel; Helmut Rinne, Lübeck, both of Fed. Rep. of Germany

[73] Assignee: Drägerwerk Aktiengesellschaft, Fed. Rep. of Germany

[21] Appl. No.: 858,447

[22] Filed: Dec. 7, 1977

[30] Foreign Application Priority Data
Dec. 7, 1976 [DE] Fed. Rep. of Germany ....... 2655318

[51] Int. Cl.² ........................................... G01N 27/46
[52] U.S. Cl. .................................................. 204/195 P
[58] Field of Search .................. 204/1 Y, 1 P, 195 P, 204/195 M, 195 S, 195 R; 324/29

[56] References Cited
U.S. PATENT DOCUMENTS

| 3,719,564 | 3/1973 | Lilly et al. ..................... 204/195 S X |
| 4,020,830 | 5/1977 | Johnson et al. ................. 204/195 M |
| 4,040,929 | 8/1977 | Bauer ............................... 204/195 S |

FOREIGN PATENT DOCUMENTS
2501399  7/1976  Fed. Rep. of Germany ............. 324/29

Primary Examiner—G. L. Kaplan
Attorney, Agent, or Firm—McGlew and Tuttle

[57] ABSTRACT

Measuring probe for a polarographic determination of gas partial pressures in aqueous, and more particularly in biologic, medium, comprises at least a part made up of a plurality of thin films including a polarographic surface having a diffusion film membrane which applies directly on at least the polarographing surface, and wherein at least the film material contiguous to the polarographing surface comprises a thin film of an inorganic insulating material.

4 Claims, 4 Drawing Figures

POLAROGRAPHIC MEASURING PROBE WITH DIFFUSION FILM MEMBRANE

BACKGROUND OF THE INVENTION

1. Field of the Invention

The invention relates in general to the construction of measuring probe and in particular to a new and useful measuring probe for the polarographic determination of gas partial pressures in aqueous, more particularly biologic, medium, which includes at least a part made up of thin films, and where a diffusion film membrane applies directly on at least the polarographic surface.

2. Description of the Prior Art

Such probes, which are used in particular for $pO_2$ determination, are described in DT-OS 2,501,399, W. Siu (Master Thesis, University of Toronto, Institute of Biomedical engineering) "Design optimization and fabrication of integrated circuit multicathode oxygen electrodes" and H. Baumgärtl and D. W. Lübbers, article "Platinum needle electrode for polarographic measurement of oxygen and hydrogen" in "Oxygen Supply", published by Urban and Schwarzenberg, 1973, p. 130.

In these probe constructions, a membrane must be arranged between the polarographic electrode (the cathode in the case of $pO_2$ measuring probes) and the medium in which the gas pressure is to be determined, at least when such probes are to be used in flowing liquids or, for example, liquids containing proteins, such as blood and other body fluids. It is the function of the membrane to let, apart from the gas to be measured, only those substances get from the medium to the polarographic surface, which do not influence the polarographic reaction, also, as an impediment of diffusion for the gas to be measured. It is the function of the membrane to lower the gas consumption of the polarographing surface to the extent that in the medium before the membrane only a negligibly small gas diffusion field builds up.

The gas pressure gradient forming, before any polarographing surface is displaced out of the surrounding medium into the membrane, almost completely when the diffusibility for the gas to be measured is more than one order of magnitude less in the membrane than in the surrounding medium. The quantity of gas reaching the polarographing surface, to which the polarographic current, or the measuring signal, is proportional, is then determined only by the gas pressure gradient above the membrane. The gas pressure gradient above the membrane corresponds to the gas pressure in the medium, because zero gas pressure prevails on the polarographing surface. Such probes, therefore, are free of stir effect, i.e. they indicate the gas pressure in the medium independently of flows in the medium.

In oscillographic polarography (rhythmic conduction of the polarographic process), the membrane has in principle the same functions, even though in such a use a stationary diffusion field does not build up in the membrane.

A comprehensive analysis of the gas diffusion in such membranes has been given for example by C. Schneiderman in the dissertation "Arterial wall oxygen transport system: Computer simulation and experimental study, including a theoretical analysis of various tissue oxygen microelectrodes" at the University of Evanston, Illinois, 1975.

Membranes on polarographing surfaces are subjected to considerable chemical loads. In oxygen polarography, for example, $H_2O_2$ and hydroxyl ions occur as reaction products of the oxygen at the polarographing surface. It must be possible to diffuse these reaction products away through the membrane. In addition, this reaction requires water, which it must be possible to diffuse in from the medium together with the oxygen to be measured.

As membrane materials organic polymers have been used heretofore, for example, PTFE, polystyrene, polyethylene, acrylates, and many other plastics. The major disadvantage in the use of such plastics is their insufficient chemical stability to water and the products occurring in polarography. In the practice, plastics do not reach a sufficiently stable swelling equilibrium. Besides, the swelling equilibrium of the plastics depends on the concentration of resulting reaction products during the measurement. In the measuring practice, this results in the following problems:

1. Before it can be used for the measurement, the probe must be brought into swelling equilibrium with water for a prolonged time. This process takes hours or days, depending on the plastic and membrane thickness.

2. Before each measurement, calibration of the probe is necessary.

3. During prolonged measuring periods, the measurement indications of such probes drifts for a given gas pressure.

These disadvantages of plastic membranes can be reduced by making them relatively thick, in order to reduce the gas consumption and hence damage to the membrane by reaction products, and possibly by enriching the membrane with swelling agents in order to reach a relatively stable swelling state sooner. Also tests have been made to improve the membrane properties by incorporation of functional groups into the polymers.

SUMMARY OF THE INVENTION

The present invention provides a probe which is free of drift and is simple in construction. According to the invention at least the membrane material contiguous to the polarographing surface is an inorganic insulating material which is applied as a thin film on the probe. Inert inorganic insulation materials, as for example $SiO_2$ or $Si_3N_4$, show as membrane materials a much stabler swelling behavior than organic polymers. However, the diffusibility for gases, e.g. oxygen, in inorganic insulating materials is sufficiently great only if the latter are applied as a thin film and if, in applying it, provision is made for an ultra-microscopic porosity. By controlled inclusion of extraneous gas during growth of the thin film and by freezing in improbable structural states of the material it is possible, for example, to increase the diffusion coefficient for gases and water by orders of magnitude. Only by the use of thin film techniques is it possible to combine the swelling stability of inert inorganic insulating materials necessary for a membrane material with a sufficiently high diffusibility. In fact, unless they have been made, they must be heated to several hundred degrees to be able to assume the function of diffusion membranes, for example, as vacuum windows in front of mass spectrometers, in the thicknesses that can still be handled technically. Further, the thin film technique offers the possibility of a high reproducibility of the essential membrane properties such as thickness, degree of porosity and composition. The probes will then no longer have to be calibrated singly. Since in the production of thin film probes inorganic insulating materials are processed anyway, although under different precipitation conditions, the manufacturing process of the membrane fits perfectly into that of the thin film probe.

The probe of the invention is further advantageously characterized in that the membrane material is composed of several components, at least one of the components being stable to watering, while at least one of the other components is water-soluble or well hydratable. By the use of thin film techniques it is possible to produce highly improbably mixed substances. It is thus readily possible to let a watering-stable insulator skeleton be filled with ultra-microscopic fineness by a substances well soluble in water. Such a structure is produced, for example, by depositing silicon nitride on the probe simultaneously with small quantities of sodium chloride. Such a probe changes over to the hydrated state ready for measurement immediately, even if it had previously been stored dry for months. The dry storage of such probes is absolutely necessary, because the insulators necessarily used in thin film probes in other parts of the probe construction must not be kept moist for weeks.

The probe of the invention is further advantageously characterized in that the various components are different compounds of the same metal. The application of such a membrane is especially simple due to the fact that in the present state of reactive thin film technique it is readily possible to let two different reactions of a metal take place on the thin film substrate as the metal is being deposited. By suitable selection of the metal it is possible to produce, in this manner, a mixed substance which very quickly reaches a stable swelling equilibrium after watering of the probe. Compared with a membrane into which gases were incorporated in a controlled manner, such a membrane can be produced at much less cost of thin film technology.

The probe of the invention is further advantageously characterized in that one component of the membrane material is an oxide of Al, Bi, Ta, Si, Zr or Ti or a nitride of Si, Zr or Ti. It has been found in the practice that, compared with other oxides and nitrides, these oxides and nitrides are especially suitable for forming a watering-stable, possibly hydratable membrane skeleton. This is true in particular when using oxygen polarographing electrodes. With these substances as a membrane skeleton, sufficiently long, undisturbed measuring periods are possible for thin film measuring probes.

The probe of the invention is further advantageously characterized in that the membrane material is either $SiO_xN_y$, $NbO_xN_y$, $TaO_xN_y$ (or $TiO_xN_y$). The four named mixed substances are easy to produce and show very good membrane properties without admixture of other substances. The membrane material is advantageously a zeolite. Zeolites can be produced with pore sizes which ensure optimum watering at high selectivity in particular for $O_2$ and $OH^-$.

A metallic thin film is advantageously deposited on the membrane. By the application of a metallic thin film the selectivity of the membrane can be increased. Moreover, a metallic thin film of sufficient thickness offers protection of the insulator part of the membrane and of the polarographing surface against ions which are apt to disturb the polarographic process. This is valuable especially in biologic media. Moreover, it is possible, when applying an additional metallic thin film, to increase the pore size in the insulator part of the membrane, the thickness of this membrane section can be increased.

This is of advantage when the polarographic probe must be operated at comparatively high voltages, as for instance in oxygen polarography on gold cathodes. It is true also of metallic thin films that the diffusibility for gases and water or water vapor can be varied by orders of magnitude by suitable measures during depositing.

The probe of the invention further advantageously connects the metal film as a counter-electrode in an area of the probe disposed away from the measuring point. If, in addition to its function as membrane, the metal film assumes also the function of a counter-electrode, a considerable simplification results for the probe structure lying below it. The probe structure below need then consist only of a polarographing electrode which is covered by an insulator at the points where the polarographic reaction is not to take place. Another advantage results due to the fact that the electric field is developed uniformly in the membrane plane and a variation of the ionic strength in the medium to be measured can have no effect on the active pole voltages.

The probe metal film material is advantageously silver, palladium or niobium. In particular for oxygen polarography, silver is suitable as material outwardly adhering to the insulator portion of the membrane. Even at a moderate degree of loosening of the thin film, silver attains a high oxygen diffusibility, even in thicknesses over 500 angstrom. Thus silver is especially well suitable for the protection of the thin films lying below. Moreover, in oxygen polarography a silver anode makes possible an especially marked development of the polarographic plateau. The probe thus becomes especially unsusceptible to shifts in the active pole voltage, as may result at very high oxygen pressures. Like silver, niobium is also suitable to ensure sufficient oxygen and water passage through the membrane in oxygen polarography, and also at very great layer thicknesses of over 1000 angstrom. The advantages described for silver in oxygen polarography apply analogously to the use of palladium in hydrogen polarography.

Accordingly, it is an object of the invention to provide a measuring probe for the polarographic determination of gas partial pressures in aqueous and particularly in biologic medium, which comprises at least a part made of a plurality of thin films, including a polarographic surface having a diffusion film membrane applied directly on at least the polarographic surface, wherein at least the film material contiguous to the polarographic surface comprises a thin film of an inorganic insulating material. A further object of the invention is to provide a measuring probe which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
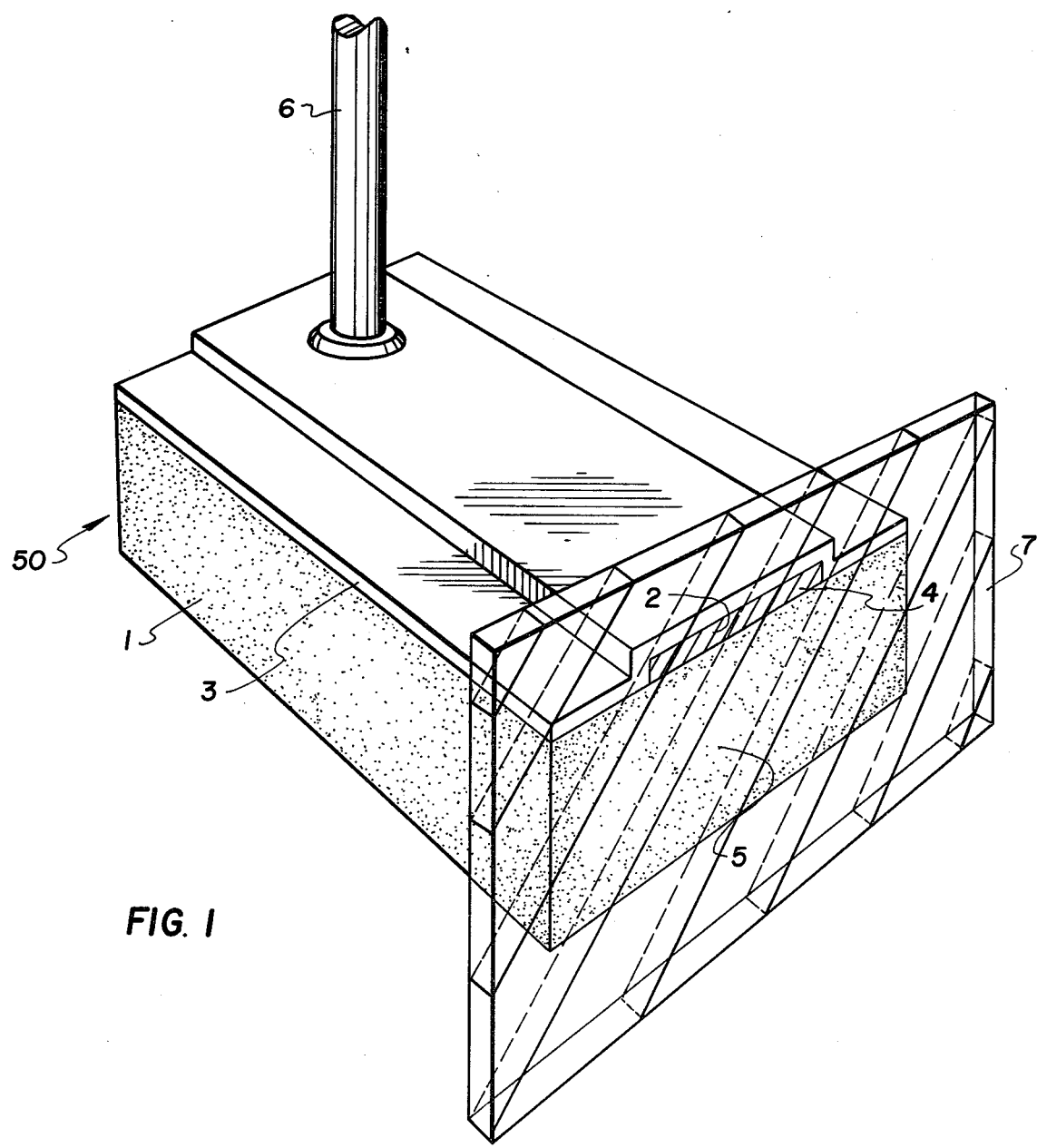
FIG. 1 is a front top perspective view of a probe constructed in accordance with the invention.

Referring to the drawings in particular, the invention embodied therein in FIG. 1 comprises a probe generally designated 50 with a diffusion membrane 7 directly applying an an active surface 5 of the probe. The membrane is shown not as a film covering the probe body but as a disk arranged before the active surface of the probe in order to show the invention in a simple form.

A metal film 2 is arranged on an insulating support body 1. The film 2 is contacted through a contact wire 6. With the exception of the area in the active surface 5 of the probe in which the metal film as polarographing electrode enters into electrochemical contact with the surrounding medium across the membrane 7, the metal film 2 is covered on all sides by a film 3 of insulating material against the surrounding medium. The polarographically active surface of the metal film 2 is formed as cut edge 4 of the metal thin film 2. The material of the metallic thin film 2 is determined by the type of polarographic reaction desired. To close the polarographic measuring circuit across the diffusion membrane 7, a counter-electrode (not shown) is located in the medium surrounding the probe.

Figure 2:
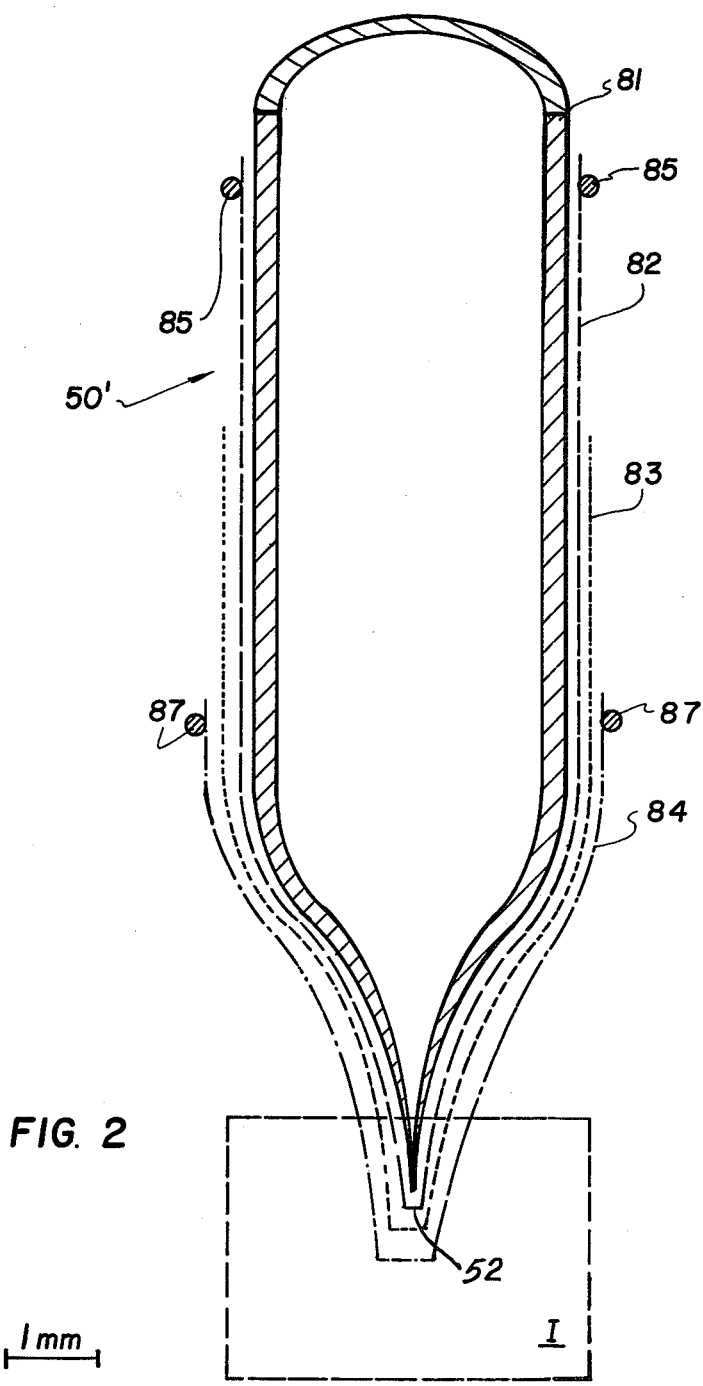
FIG. 2 is a view similar to FIG. 1 of another embodiment of the invention with two electrodes arranged on a pointed support body.

FIG. 2 shows a section through a pointed oxygen-measuring probe generally designated 50', which is divided into a contact area with the contact wires 87 and 85, located at the shank, and a tip area. The tip area of the probe is introduced into the medium in which the gas pressure is to be determined. With such a probe, oxygen, for example, can be polarographed for example in blood vessels or also in parenchymatour organs. To be able to use such a probe in the practice, the contact area at the shank must be closed off liquidproof from the medium to be measured in a manner not shown.

A gold film 82 is applied directly on a support body 81 of the oxygen measuring probe 50' forming a measuring electrode. It has a thickness of about 1000 angstrom. The gold film 82 is contacted by the contact wire 85. On the gold film 82 is applied an insulating film 83, which leaves the gold film free in the contact area adjacent contact wires 85 and 87 and in the tip area of the measuring point. The tip gap 52 in the covering of the gold film 82 is only schematically represented, however, as it is microscopically small in the scale of the drawing. The insulating film 83 has a thickness of a little over 1 micron. It consists of a dense, water-insensitive dielectric.

On the insulation film 83 lies a diffusion membrane 84. However, in the contact area of the probe between contacts 85 and 87, membrane 84 ends earlier than the insulation film 83. The membrane 84 is composed of a lower layer of an inorganic insulating material and an upper layer of a metallic thin film. This upper layer is electrically contacted by the contact wire 87. To ensure the electric insulation between the oxygen polarographing gold electrode 82 and the silver layer of the membrane functioning as counter-electrode in the contact area, the surface dielectric strength of the insulation film 83 must be ensured by suitable protective measures. At any rate, depending on the size of the polarographing aperture and depending on the diffusibility of the membrane thin film 84, the resistance between the two electrodes must be in the non-polarographing state for example before start of measuring in a range of up to $10^{12}$ ohm.

Figures 3A, 3B:
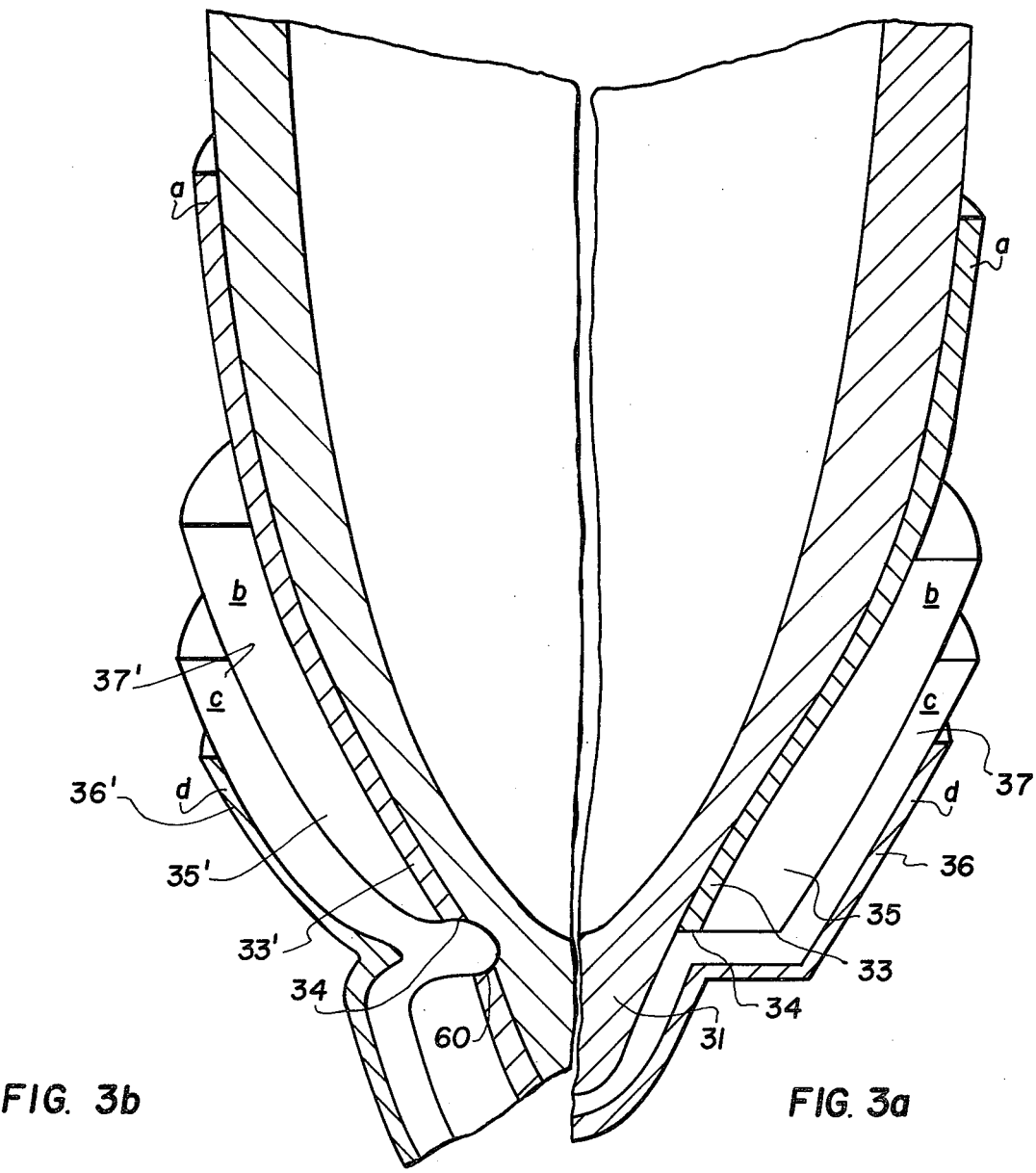
FIG. 3a is a partial sectional view similar to FIG. 2 of another embodiment of the invention.
FIG. 3b is a view similar to FIG. 3a of still another embodiment of the invention.

FIGS. 3a and 3b show two embodiments on a greatly enlarged scale of a tip region I similar to FIG. 2, with the two embodiments illustrated as right and left half portions in the respective figures. It should be noted that for reasons of representability the film thickness is increased by orders of magnitude relative to the thickness of the probe carrier or support shown hatched.

The two tip designs illustrated in FIGS. 3a and 3b exhibit the same layer composition with, from inside to outside, the layers a, b, c and d. Different are only the configurations of the polarographing measuring surfaces arranged in the tip region.

The design form shown in FIG. 3a has an insulating film 35 over a gold film 33 serving as measuring electrode. These two films are removed in the tip region at 34. Above this arrangement is disposed directly the diffusion film membrane consisting of an inner film 37 of an inorganic insulation material and an outer film 36 of silver, which brings about the external closing off of the probe.

The polarographing measuring area of the gold film 33 thus exists at 34, where the gold film is in contact with the diffusion membrane consisting of the films 37 and 36. This measuring area or polarographing surface acts as the cathode surface for the instrument. In the embodiment of FIG. 3a the measuring point 34 surrounds the probe tip annularly. The embodiment in FIG. 3b shows another design, where not the entire tip region of the layers 33' and 35' is removed but merely at one point a pore 60 is formed in which the gold film 33 is in contact with the diffusion membrane.

The insulation film 35' comprises a thin film of a dielectric optimized as to density, watering stability and high insulation capacity. This insulator must meet especially high requirements because the polarographic current of this probe is only about $10^{-9}$ A for example in air-saturated solution. Slight leak currents between the polarized metal films 36 and 33, as conceivable for instance through a pinhole in the insulation film 35 in the shank region of the probe, will greatly falsify the measured value.

The inorganic film 37 of the diffusion membrane formed of the films 36 and 37 comprise for example essentially silicon nitride. During application of this silicon nitride, sodium chloride, for example, is deposited on the probe simultaneously at a low rate. This results in a mixed substance which very quickly reaches a stable swelling equilibrium despite the long dry storage period between the production of the probe and its use.

The microporosity of the silver film 36 is determined during its deposition depending on its desired thickness and the desired oxygen consumption data. By temperature conduction of the probe, possibly in connection with variations of the residual gas composition and the degree of ionization thereof, it is readily possible by modern thin film techniques to carry out such high porosity variations.

While specific embodiments of the invention have been shown and described in detail to illustrate the application of the principles of the invention, it will be understood that the invention may be embodied otherwise without departing from such principles.

What is claimed is:

1. A measuring probe comprising a support body having a tip, a first metal electrode film overlying said support, an insulation film overlying a major portion of said first metal electrode film, an inner film of inorganic insulation material overlying said insulation film, a second metal electrode film overlying said insulation film, said first metal electrode film having an annular edge defining a measuring point around said tip, at least said inorganic insulation film covering said measuring point, said second metal electrode being separated from said first metal electrode film at least by said inner film of inorganic material, said first metal film ending in an annular edge around said tip covered by said inorganic insulation material, said inorganic insulation material selected from the group consisting of an oxide of Al, Bi, Ta, Si, Zr, or Ti; or a nitride of Si, Zr or Ti.

2. A measuring probe as defined in claim 1 wherein said second metal electrode film consists of a material selected from the group of silver, palladium and niobium.

3. A measuring probe according to claim 1, wherein said inorganic insulating film is selected from the group consisting of $SiO_xN_y$, or $TiO_xN_y$ where $O \leqq x \leqq 2$ and $O \leqq y \leqq 1.33$; and the $NbO_xN_y$ and $TaO_xN_y$ where $O \leqq x \leqq 2.5$ and $O \leqq y \leqq 1$.

4. A measuring probe comprising a support body having a tip, a first metal electrode film overlying said support, an insulation film overlying a major portion of said first metal electrode film, an inner film of inorganic insulation material overlying said insulation film, a second metal electrode film overlying said inorganic insulation film, said first metal electrode film having an annular edge defining a measuring point around said tip, at least said inorganic insulation film covering said measuring point, said second metal electrode being separated from said first metal electrode film at least by said inner film of inorganic insulation material, a pore formed on said inner film of an inorganic insulation material, said insulating film and said second metal electrode which are compressed inwardly into said first metal electrode film to the support body, said inorganic insulating film selected from the group consisting of an oxide of Al, Bi, Ta, Si, Zr, or Ti; or a nitride of Si, Zr, or Ti.

* * * * *